United States Patent
Jones

(10) Patent No.: US 12,343,068 B2
(45) Date of Patent: Jul. 1, 2025

(54) ELECTROSURGICAL INSTRUMENT

(71) Applicant: GYRUS ACMI, INC., Bartlett, TN (US)

(72) Inventor: Lewis Jones, Cardiff (GB)

(73) Assignee: GYRUS ACMI, INC., Bartlett, TN (US)

( * ) Notice: Subject to any disclaimer, the term of this patent is extended or adjusted under 35 U.S.C. 154(b) by 603 days.

(21) Appl. No.: 16/164,224

(22) Filed: Oct. 18, 2018

(65) Prior Publication Data

US 2019/0133675 A1     May 9, 2019

(30) Foreign Application Priority Data

Oct. 18, 2017  (GB) ..................................... 1717109

(51) Int. Cl.
| | | |
|---|---|---|
| A61B 18/14 | (2006.01) | |
| A61B 17/29 | (2006.01) | |
| A61B 18/00 | (2006.01) | |
| A61B 18/12 | (2006.01) | |
| A61B 90/00 | (2016.01) | |

(52) U.S. Cl.
CPC .. *A61B 18/1447* (2013.01); *A61B 2017/2925* (2013.01); *A61B 2018/00083* (2013.01); *A61B 2018/00107* (2013.01); *A61B 2018/00607* (2013.01); *A61B 2018/0063* (2013.01); *A61B 2018/126* (2013.01); *A61B 2018/1455* (2013.01); *A61B 2090/035* (2016.02)

(58) Field of Classification Search
CPC .............. A61B 18/085; A61B 18/1442; A61B 18/1445; A61B 18/1447; A61B 2018/00607; A61B 2018/0063; A61B 2018/126; A61B 2018/1452; A61B 2018/1455

USPC .................................. 606/37, 41, 48, 50–52
See application file for complete search history.

(56) References Cited

U.S. PATENT DOCUMENTS

| | | | |
|---|---|---|---|
| 7,473,253 B2 * | 1/2009 | Dycus | ................ A61B 18/1445 606/51 |
| 8,241,284 B2 | 8/2012 | Dycus et al. | |
| 10,485,607 B2 * | 11/2019 | Strobl | ................ A61B 18/1445 |

(Continued)

FOREIGN PATENT DOCUMENTS

| | | |
|---|---|---|
| EP | 2 990 189 A1 | 3/2016 |
| EP | 3 251 623 A1 | 12/2017 |
| WO | 2017/189402 A1 | 11/2017 |

OTHER PUBLICATIONS

Mar. 8, 2018 Search Report issued in European Patent Application No. GB1717109.1.

*Primary Examiner* — Thomas A Giuliani
(74) *Attorney, Agent, or Firm* — Oliff PLC

(57) ABSTRACT

An electrosurgical instrument includes a handle including an actuating mechanism movable between a first position and a second position, and a pair of opposing first and second jaw members. A first sealing electrode is located on an inner surface of the first jaw member, and a second sealing electrode is located on an inner surface of the second jaw member. A plurality of stop members are longitudinally disposed on one or both of the inner surfaces of the jaw members, and at least two of the plurality of stop members are of different heights such that the first and second jaw members flex when moved to their closed position such that the distance between the first and second sealing electrodes is non-uniform.

16 Claims, 3 Drawing Sheets

(56) References Cited

U.S. PATENT DOCUMENTS

Figure 1:
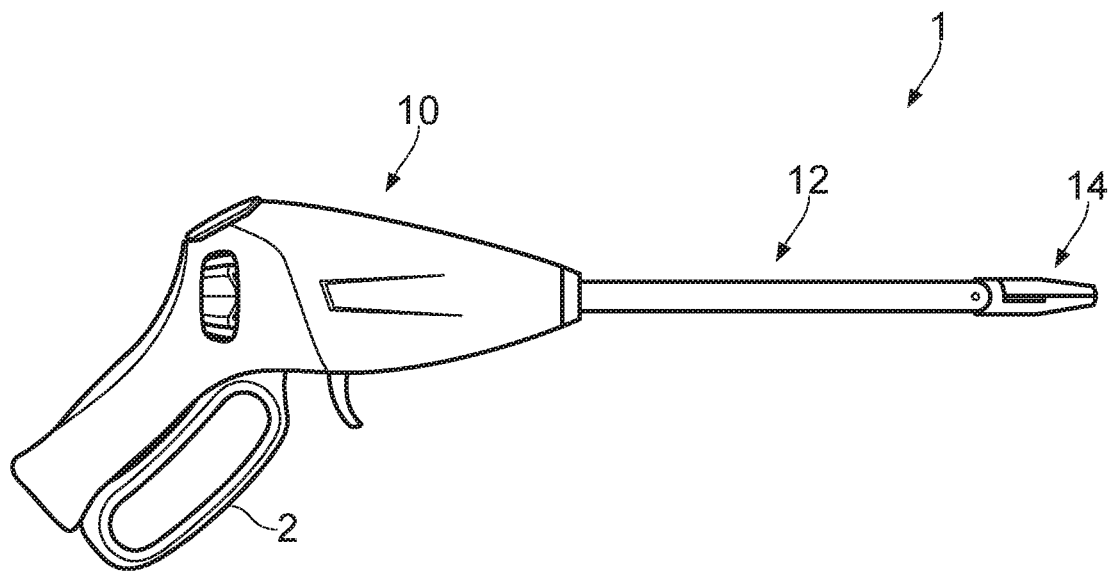

| | | | |
|---|---|---|---|
| 2006/0041254 A1* | 2/2006 | Francischelli | A61B 18/1445 606/41 |
| 2006/0224158 A1* | 10/2006 | Odom | A61B 18/1445 606/171 |
| 2007/0156140 A1 | 7/2007 | Baily | |
| 2010/0249776 A1* | 9/2010 | Kerr | A61B 18/1445 606/51 |
| 2014/0371743 A1 | 12/2014 | Rothweiler et al. | |
| 2017/0312018 A1* | 11/2017 | Trees | A61B 18/1445 |
| 2017/0312019 A1* | 11/2017 | Trees | A61B 18/1445 |

\* cited by examiner

ELECTROSURGICAL INSTRUMENT

This application claims priority to United Kingdom Patent Application No. 1717109.1, filed Oct. 18, 2017. The contents of that application are incorporated by reference herein.

This invention relates to an electrosurgical instrument for sealing tissue, and to a jaw for such an instrument. Such systems are commonly used for the treatment of tissue in surgical intervention, most commonly in "keyhole" or minimally invasive surgery, but also in "open" surgery.

It is known to provide an electrosurgical instrument in which the sealing of tissue is effected by means of a pair of jaw elements, U.S. Pat. Nos. 7,473,253 & 8,241,284 are two examples of this kind of instrument. These two patents describe the provision of one or more non-conductive stop members, in order to regulate the spacing between the jaws when tissue is held therebetween. The present invention attempts to provide an improvement to an arrangement instrument such as this.

Accordingly, an electrosurgical instrument is provided, the electrosurgical instrument including
a handle including an actuating mechanism movable between a first position and a second position,
a pair of opposing first and second jaw members, the first and second jaw members each having an inner surface, movement of the actuating mechanism from its first position to its second position causing at least one of the jaw members to move relative to the other from a first open position in which the jaw members are disposed in a spaced relation relative to one another, to a second closed position in which the jaw members cooperate with their inner surfaces adjacent one another,
a first sealing electrode located on the inner surface of the first jaw member,
a second scaling electrode located on the inner surface of the second jaw member,
electrical connections capable of connecting the instrument to an electrosurgical generator, such that when the jaw members are in their closed position with tissue grasped therebetween, the instrument is capable of sealing the tissue by passing an electrosurgical current into the tissue from the first and second sealing electrodes,
a plurality of stop members longitudinally disposed on one or both of the inner surfaces of the first and second jaw members, at least two of the plurality of stop members being of different heights such that the first and second jaw members flex when moved to their closed position such that the distance between the first and second sealing electrodes is non-uniform.

It will be appreciated that the first and second sealing surfaces may be constituted by electrically conductive components, such as electrodes or metallic shims, attached to the inner surfaces of the jaw members. Alternatively, the first and second jaw members may be formed from an electrically conductive material, in which case the inner surfaces of the jaw members may themselves constitute the first and second sealing surfaces. Whichever arrangement is employed, the difference in heights of the stop members ensures that the jaw members flex when closed one against the other, such that the distance between the first and second sealing surfaces is non-uniform.

According to a convenient arrangement, the stop member which is positioned most distally has a height greater than that of at least one of the remaining stop members, and preferably a height greater than that of all of the remaining stop members. In this way, the distal stop member is positioned to cause bending of the jaw member such that the jaws come together firstly towards their distal end, and then progressively along their length in a proximal progression. This progressive contact will hereby be called a "toe-in" progression.

Conveniently, the plurality of stop members include at least three stop members each of differing heights, and conceivably at least four stop members each of differing heights. Typically, the plurality of stop members include more than four stop members, but with at least for stop members each of differing heights. Conceivably, the plurality of stop members include more than five stop members, but with at least four stop members each of differing heights. By designing the stop members with differing heights, the jaw can be arranged such that the stop members come into operation in a progression, starting with the distal stop member and progressing sequentially in a proximal direction. A benefit of this progression is that smaller stops can be employed without the risk of crushing tissue grasped between the jaws.

The construction of the jaw members is such that, for the magnitude of the load applied between the jaw members, the distortion of the jaw members under load is similar in magnitude to the difference in the heights of the stop members. In this way the jaw members can apply the full force to thick bundles of tissue while reducing the load on smaller stop members and on smaller vessels.

The plurality of stop members are preferably provided in pairs of stop members, laterally spaced with respect to the jaw members. According to a convenient arrangement, at least one of the jaw members is provided with a track for a cutting blade, the track running longitudinally along the jaw member. Where the stop members are provided in pairs, the pairs of stop members are conveniently provided one on each side of the longitudinal track. This helps to balance the forces applied to the jaw members, and helps to prevent twisting of the jaw members as they close. Conveniently, the stop member which is positioned most distally is a single stop member positioned at the end of the longitudinal track.

Preferably, the plurality of stop members are formed from a rigid material such that they suffer linear compression of less than 2 microns. The rigidity of the stop members ensures that the spacing between the jaw members is maintained, and that the jaw members flex as previously described when a load is applied between the jaw members. The plurality of stop members are preferably also formed from an electrically non-conducting material. This simplifies the design, by allowing the stop members to come into contact with the opposite sealing surface without the concern that electrical shorting will occur. If the stop members are to be formed of electrically conductive material, then an insulation member must be provided for each stop member to ensure that such electrical shorting does not occur.

According to a preferred arrangement, at least two of the plurality of stop members are of different diameters. Not only are the stop members designed to have different heights, but different diameters as well. Preferably, the stop members which are of different diameters are also of different heights. In one convenient arrangement, the stop member which is positioned most distally has a diameter greater than that of at least one of the remaining stop members, and typically a diameter greater than that of all of the remaining stop members.

Typically, the plurality of stop members include at least three stop members each of differing diameters. In one construction, the plurality of stop members include more than five stop members, but with at least three stop members each of differing diameters.

The invention further resides in a jaw for an electrosurgical instrument, including a sealing electrode located on the inner surface of the jaw, and a plurality of stop members longitudinally disposed on the inner surface of the jaws, at least two of the plurality of stop members being of different heights, and wherein the stop member which is positioned most distally has a height greater than that of at least one of the remaining stop members. As before, the stop member which is positioned most distally conveniently has a height greater than that of all of the remaining stop members. Also as before, the stop members may vary in diameter as well as in height, just as previously described.

Figure 2A:
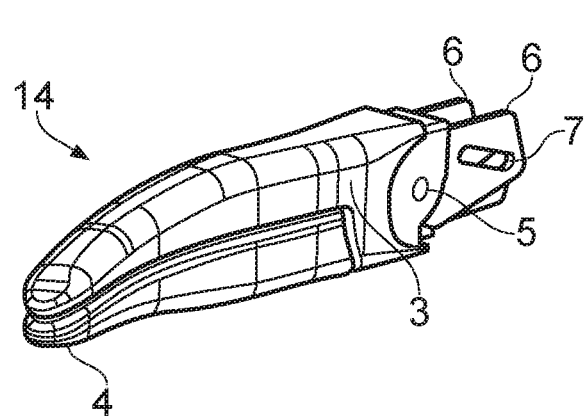
Figure 2B:
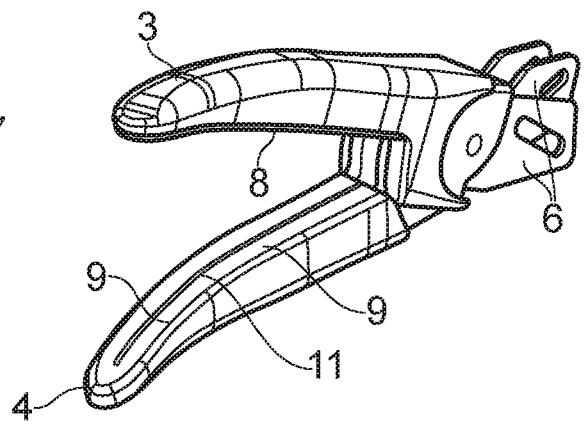
Figure 3:
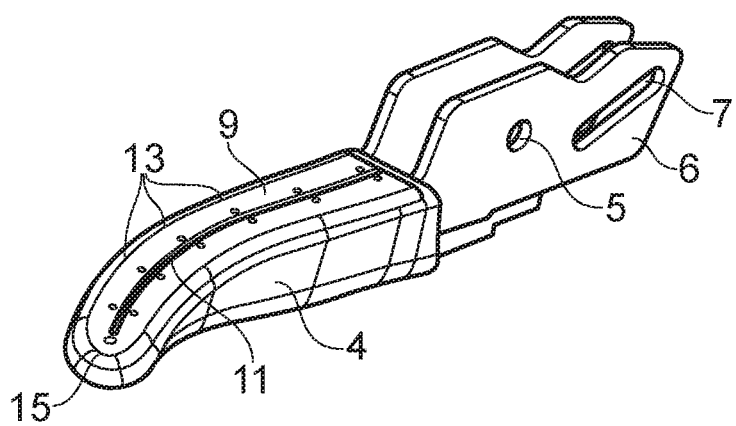
Figure 4:
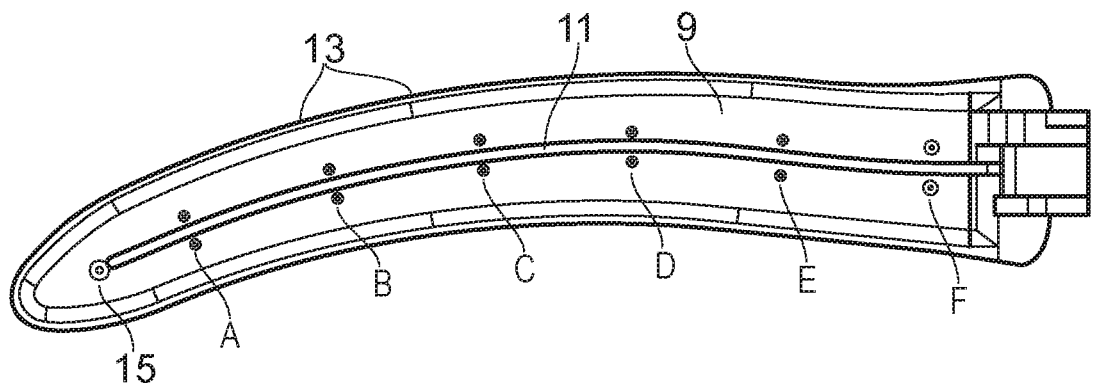
Figure 5:
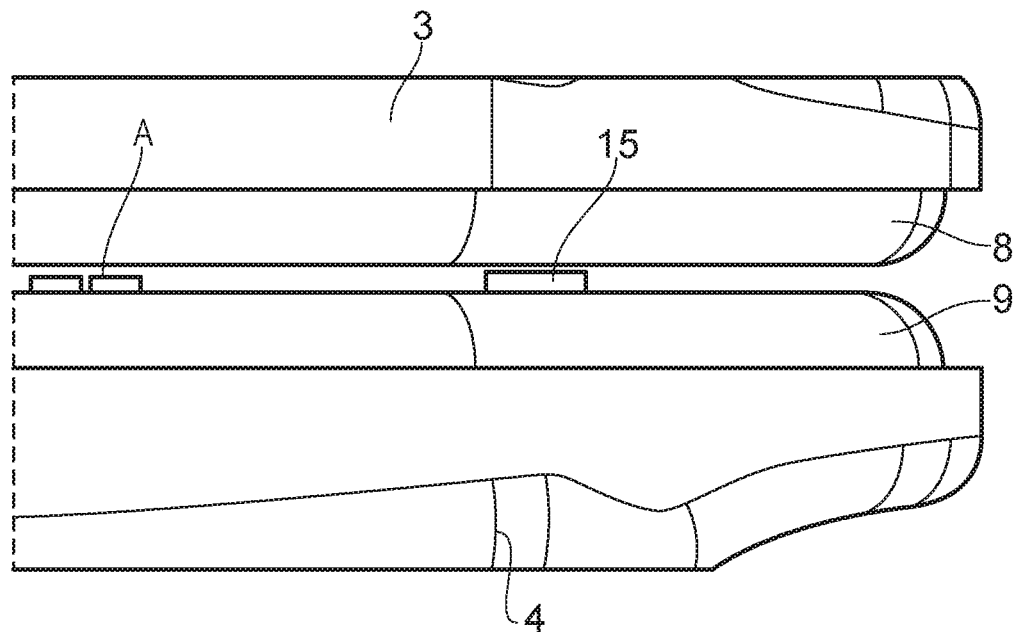
Figure 6:
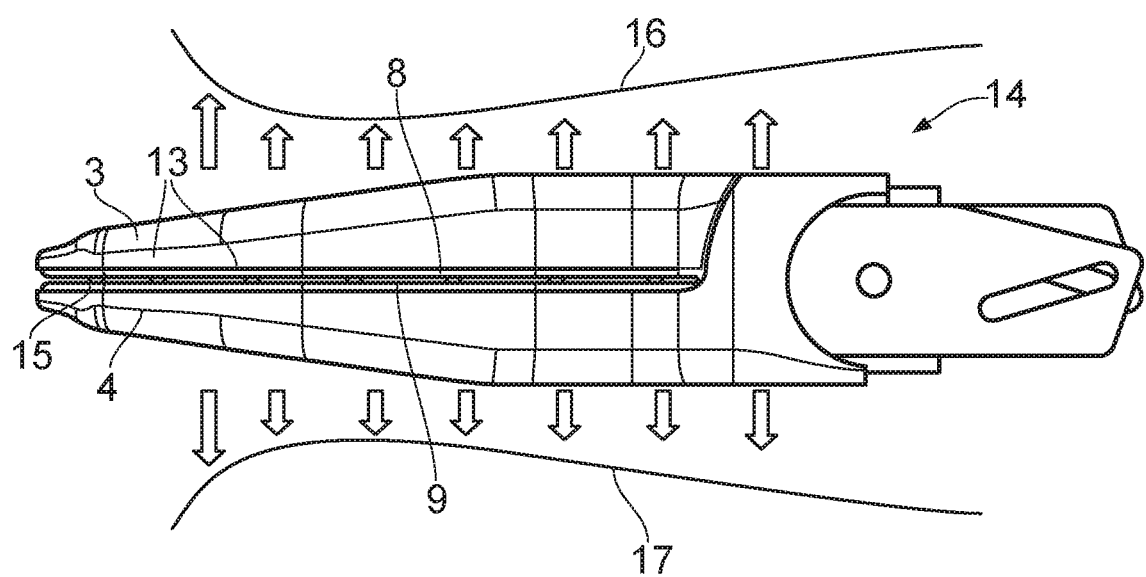

The invention will now be further described, by way of example only, with reference to the accompanying drawings, in which:

FIG. 1 is a schematic side view of an electrosurgical instrument in accordance with the present invention, FIGS. 2A & 2B are enlarged perspective views of the jaws of the electrosurgical instrument of FIG. 1, FIG. 3 is a perspective view of one of the jaws of FIGS. 2A & 2B, FIG. 4 is a plan view of the jaw of FIG. 3, FIG. 5 is an enlarged perspective side view of the jaws of FIGS. 2A & 2B, and FIG. 6 is a schematic side view of the jaws of FIGS. 2A & 2B.

Referring to FIG. 1, an electrosurgical instrument is shown generally at 1, and comprises a handpiece 10 and an elongate shaft 12. A pair of jaws 14 are present at the distal end of the shaft 12. An actuating mechanism in the form of a handle 2, movable with respect to the handpiece 10, opens and closes the jaws 14.

FIG. 2 shows the jaws 14 in more detail. The jaws 14 comprise an upper jaw 3 and a lower jaw 4, pivotable with respect to one another about a pivot 5. Flanges 6 containing cam slots 7 are used to move the jaws 14 between their open and closed positions. The closed position is shown in FIG. 2A, while the open position is shown in FIG. 2B.

A metallic shim 8 is attached to the upper jaw 3, while a similar shim 9 is attached to the lower jaw 4. The shims 8 & 9 form sealing surfaces adapted to grip tissue between the jaws, and also electrodes for the supply of electrosurgical energy to the tissue. A longitudinal channel 11 is present on the lower jaw 4 to form a track for a mechanical cutting blade (not shown). A similar channel (not shown) is present on the upper jaw 3.

FIG. 3 shows the lower jaw 4 without the upper jaw being present. The shim 9 is provided with metallic stop members 13, the stop members being provided in pairs, one either side of the channel 11. A single stop member 15 is provided at the distal end of the channel 11, located centrally.

FIG. 4 shows the stop members in more detail. Single stop member 15 is located most distally, while pairs A, B, C, D & E are located either side of the channel 11 and progressing proximally back along the jaw 4. Pairs A, B, C, D & E are the same diameter, but vary in height, with the heights being given in Table 1 below. Pair F is the most proximal pair of stop members, and are larger in both height and diameter as compared to pairs A, B, C, D & E. The stop members 13 & 15 are deposited directly on to the shim 9, typically by a printing technique.

TABLE 1

| Reference | No. of Stops | Diameter (mm) | Distance from Channel | Stop Height (μm) |
|---|---|---|---|---|
| Stop 15 | 1 | 1.2 | 0 | 175 |
| Pair A | 2 | 0.4 | 0.6 | 125 |
| Pair B | 2 | 0.4 | 0.6 | 125 |
| Pair C | 2 | 0.4 | 0.6 | 100 |
| Pair D | 2 | 0.4 | 0.6 | 100 |
| Pair E | 2 | 0.4 | 0.7 | 125 |
| Pair F | 2 | 0.6 | 0.8 | 150 |

The stop with the greatest height is stop 15. Pair F have the second greatest height, followed by pairs A, B & F. Pairs C & D have the smallest heights. Similarly, stop 15 has the greatest diameter, followed by pair F. All of the other pairs have the same diameter, less than that of stop 15 or pair F. Pairs A to D are the same distance from the channel 11, with pair E slightly further apart and pair F furthest of all.

FIG. 5 shows the distal stop members when the jaws 3 & 4 are pressed together. Being greatest in height, as the jaw members approach one another, single stop member 15 is first to contact the shim 8 on the upper jaw 3. As further closing pressure is applied by the activation of the handle 2, the jaws 3 & 4 will flex along their length as shown in FIG. 6, causing pairs A to F to come into contact sequentially with shim 8. FIG. 6 shows at 16 & 17 the bending of the jaws (exaggerated for illustrative purposes) caused by the different stop heights, such that the distance between the shims 8 & 9 is non-uniform.

The above description uses the terms "upper jaw" and "lower jaw" for ease of understanding. However, it is to be understood that the shaft 12 is rotatable with respect to the handpiece 10, such that the jaws may be present at any orientation throughout 360 degrees. Thus, either jaw may be above the other at certain times, with either jaw being the "upper jaw" at that moment in time. Also, the stop members 13 may be present solely on one jaw, or alternately on both jaws. The difference in height, diameter and spacing of the stop members 13 ensures that they engage in a sequential manner as the jaws are pressed one against the other. This means that the jaws "toe-in" one with respect to the other, with the distal part of the jaws closing before the proximal part. This allows the instrument to seal small diameter vessels as effectively as large diameter vessels or thick bundles of tissue.

The invention claimed is:

1. An electrosurgical instrument comprising
a handle including an actuating mechanism movable between a first position and a second position,
a pair of opposing and elongated first and second jaw members, each of the pair of first and second jaw members having a planar inner surface, the actuating mechanism and the pair of first and second jaw members are configured such that movement of the actuating mechanism from the first position to the second position causes at least one of the pair of first and second jaw members to move relative to another of the pair of the first and second jaw members from a first open position in which the pair of first and second jaw members are spaced apart to receive tissue between the pair of first and second jaw members to a second closed position in which the pair of jaw members are intended to grasp the tissue,
a first sealing electrode on the planar inner surface of the first jaw member, a second sealing electrode on the planar inner surface of the second jaw member,
an electrical connection configured to connect the instrument to an electrosurgical generator, the instrument being configured such that, when the pair of first and second jaw members are in the second closed position with the tissue grasped between the pair of the first and second jaw members, the instrument is capable of sealing the tissue by passing an electrosurgical current into the tissue from the first and second sealing electrodes, and
a plurality of non-conductive stop members (a) longitudinally on one or both of the planar inner surfaces of the pair of first and second jaw members and (b) that are configured to (i) stop relative movement of the pair of first and second jaw members from the first open position to the second closed position, and (ii) define a minimum space between the first sealing electrode and the second sealing electrode, wherein
the plurality of stop members includes pairs of stop members, laterally spaced with respect to the pair of first and second jaw members, at least two of the plurality of stop members are fixed height stop members with fixed heights, a fixed height of one of the at least two of the plurality of stop members being different than a fixed height of another of the at least two of the plurality of stop members, a most proximal pair of the plurality of stop members having a greater fixed height than all of the pairs of the plurality of stop members positioned distal to the most proximal pair, and
the pair of first and second jaw members and the plurality of stop members are configured such that the pair of first and second jaw members flex along longitudinal axes of the pair of first and second jaw members between longitudinal ends of the pair of first and second jaw members when moved to the second closed position and engage the tissue such that the planar inner surface of the each of the pair of first and second jaw members changes shape and a distance between the first and second sealing electrodes is non-uniform.

2. An electrosurgical instrument according to claim 1, wherein the plurality of stop members includes at least three stop members of differing heights.

3. An electrosurgical instrument according to claim 2, wherein the plurality of stop members includes at least four stop members of differing heights.

4. An electrosurgical instrument according to claim 3, wherein the plurality of stop members includes more than four stop members.

5. An electrosurgical instrument according to claim 4, wherein the plurality of stop members includes more than five stop members.

6. An electrosurgical instrument according to claim 1, wherein at least one of the pair of first and second jaw members has a longitudinal track for a cutting blade, the longitudinal track running longitudinally along the at least one of the pair of first and second jaw members.

7. An electrosurgical instrument according to claim 6, wherein one of each pair of the pairs of stop members is on each side of the longitudinal track.

8. An electrosurgical instrument according to claim 7, wherein a stop member of the plurality of stop members which is positioned most distally relative the handle is a single stop member positioned at an end of the longitudinal track.

9. An electrosurgical instrument according to claim 1, wherein each of the plurality of stop members consists of a rigid material such that the each of the plurality of stop members can be linearly compressed less than 2 microns.

10. An electrosurgical instrument according to claim 1, wherein at least a first and a second of the plurality of stop members have different diameters.

11. An electrosurgical instrument according to claim 10, wherein the at least a first and a second of the plurality of stop members have different heights.

12. An electrosurgical instrument according to claim 10, wherein the plurality of stop members includes at least three stop members of differing diameters.

13. An electrosurgical instrument according to claim 1, wherein a stop member of the at least two of the plurality of stop members that is most distal to the handle has a diameter greater than a diameter of at least one other stop member of the at least two of the plurality of stop members.

14. An electrosurgical instrument according to claim 13, wherein the stop member of the at least two of the plurality of stop members that is most distal to the handle has a diameter greater than that of all other stop members of the plurality of stop members.

15. An electrosurgical instrument according to claim 1, wherein the plurality of stop members further includes a single unpaired non-conductive stop member distal to all of the pairs of stop members.

16. An electrosurgical instrument according to claim 15, wherein the single unpaired stop member is another fixed height stop member and has a highest fixed height of all of the fixed height stop members.

* * * * *